United States Patent [19]
Leef et al.

[11] Patent Number: 5,877,186
[45] Date of Patent: Mar. 2, 1999

[54] CAROTENOID SYNTHESIS INHIBITING HERBICIDES AND FATTY ACID SYNTHESIS INHIBITING OXIME HERBICIDES AS ANTI-APICOMPLEXA PROTOZOAN PARASITE AGENTS

[75] Inventors: James L Leef, Clarksburg, Md.; Peter S. Carlson, Alexandria, Va.

[73] Assignee: ParaPRO, LLC, Carmel, Ind.

[21] Appl. No.: 985,119

[22] Filed: Dec. 4, 1997

Related U.S. Application Data

[62] Division of Ser. No. 847,932, Apr. 28, 1997.

[51] Int. Cl.⁶ .................. A61K 31/445; A61K 31/38; A61K 31/35; A61K 31/24
[52] U.S. Cl. .................. 514/315; 514/432; 514/454; 514/538
[58] Field of Search .................. 514/315, 454, 514/538, 432

[56] References Cited

U.S. PATENT DOCUMENTS 5,047,080  9/1991  Yoshida et al. .................. 71/96
5,290,696  3/1994  Somers et al. .................. 436/240.5
5,614,551  3/1997  Dick et al. .................. 514/454

Primary Examiner—Kevin E. Weddington
Attorney, Agent, or Firm—William S. Ramsey

[57] ABSTRACT

Protozoan parasites of the phylum Apicomplexa include some of the most important causative agents of human and animal diseases, in particular, malaria. The discovery that an organelle found inside parasites of this phylum probably stems from a plastid of plant origin has stimulated research on the effect of chemical herbicidal agents on Apicomplexa. Members of the triazine family and of the dinitroaniline family of herbicides have been found to be active against some Apicomplexa. The present invention extends the list of chemical herbicidal agents active against Apicomplexa to include classes of herbicides active as carotenoid synthesis inhibitory agents in plants and herbicidal agents effective against fatty acid synthesis in plants.

6 Claims, 4 Drawing Sheets

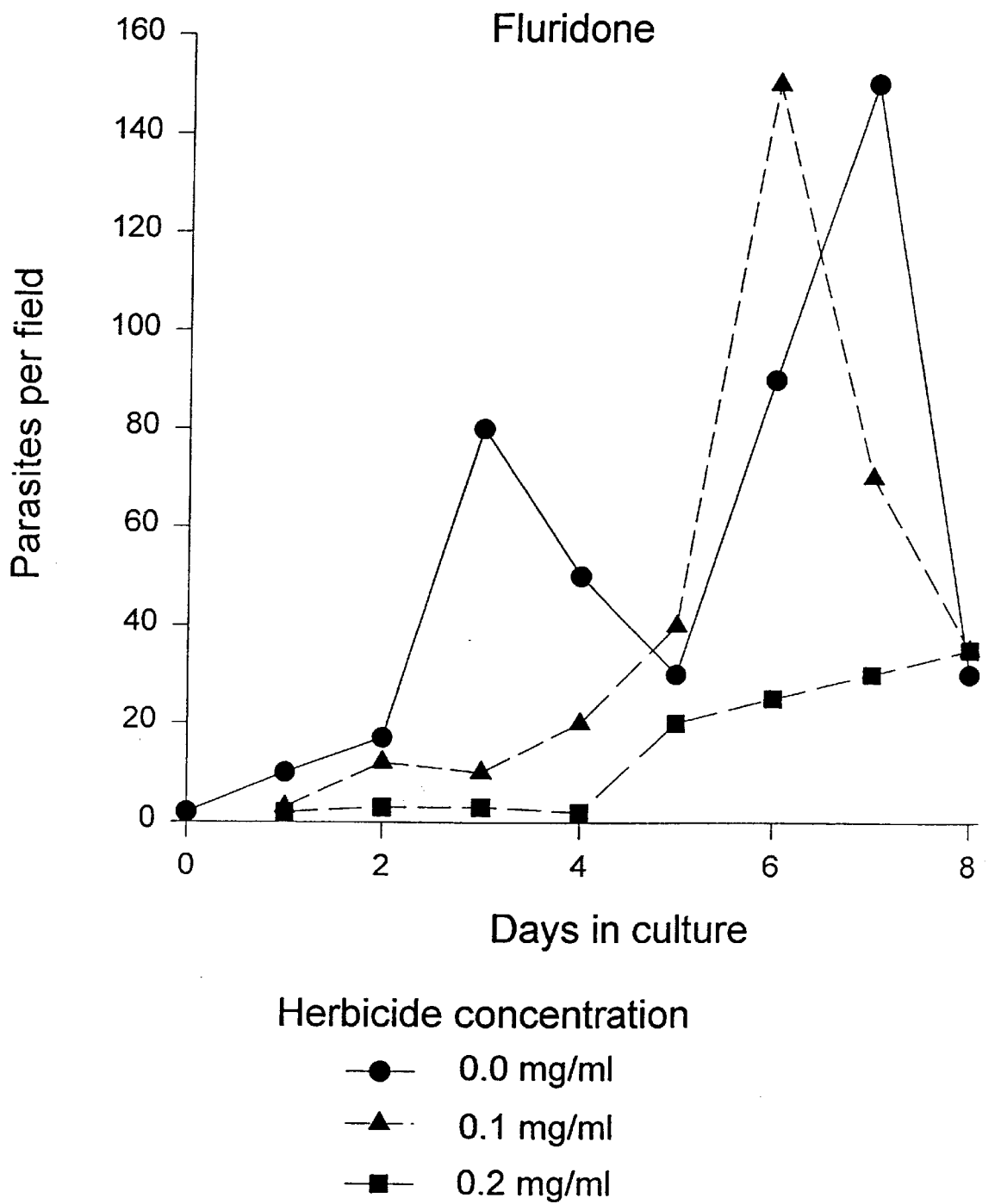

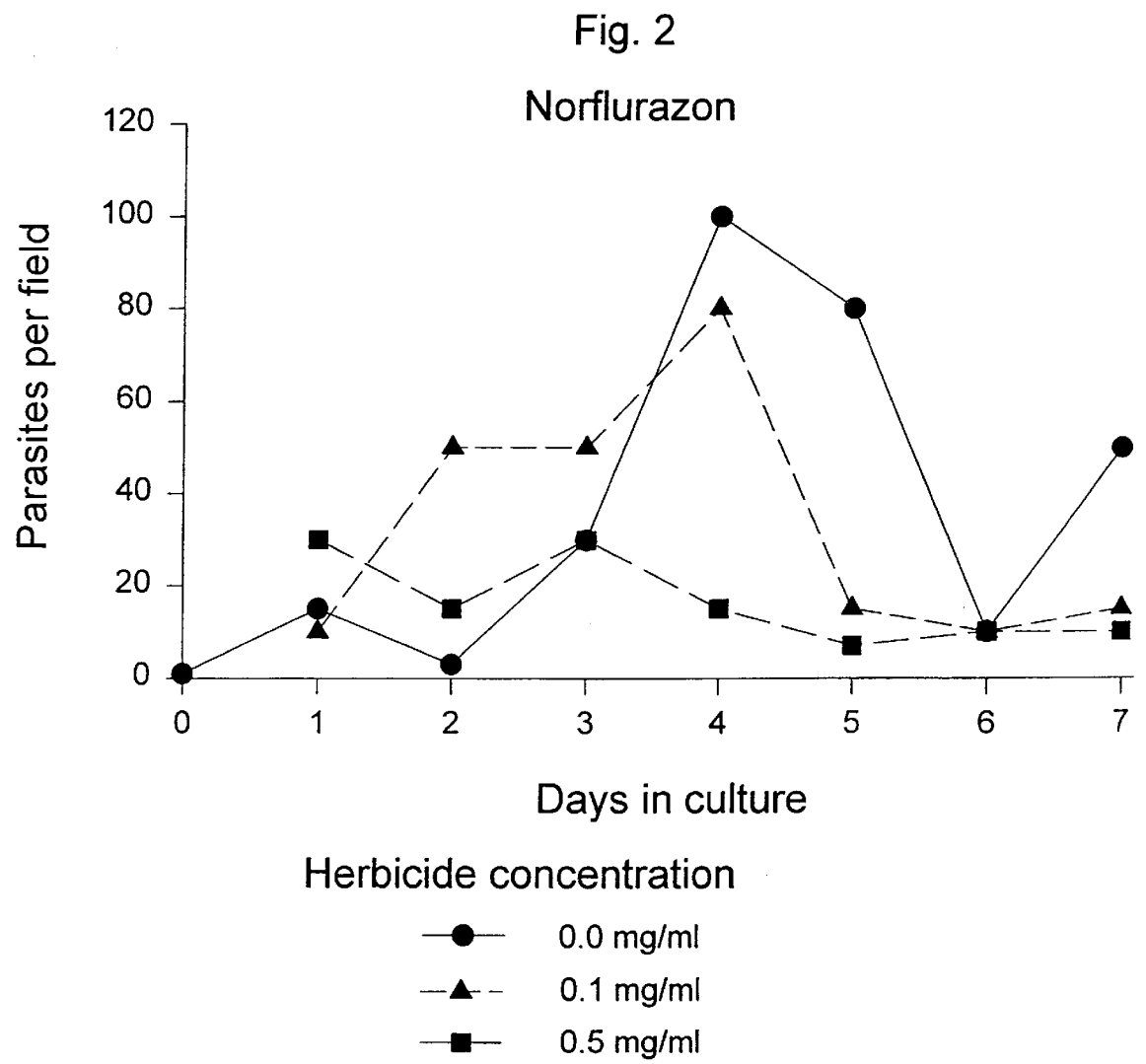

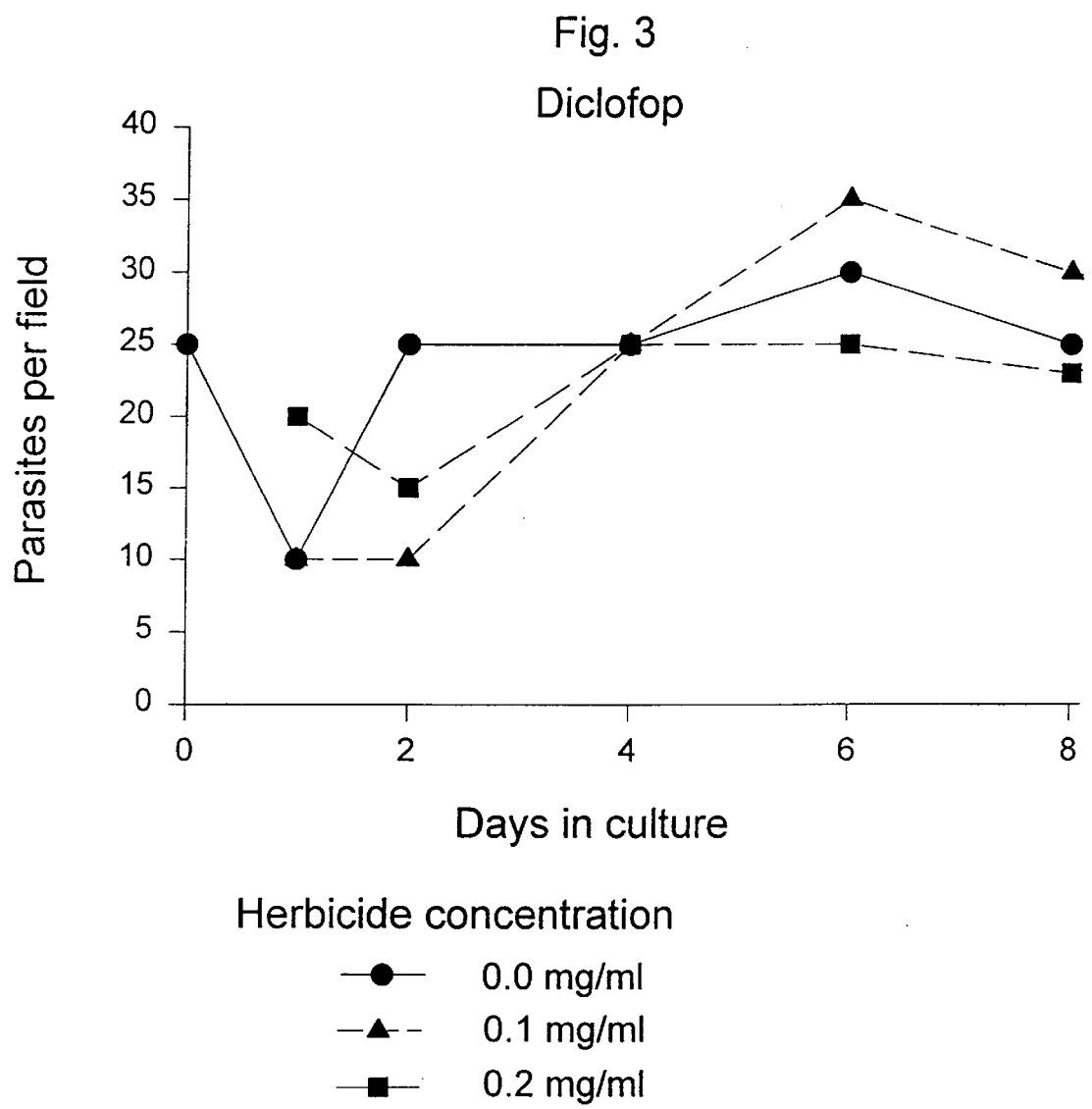

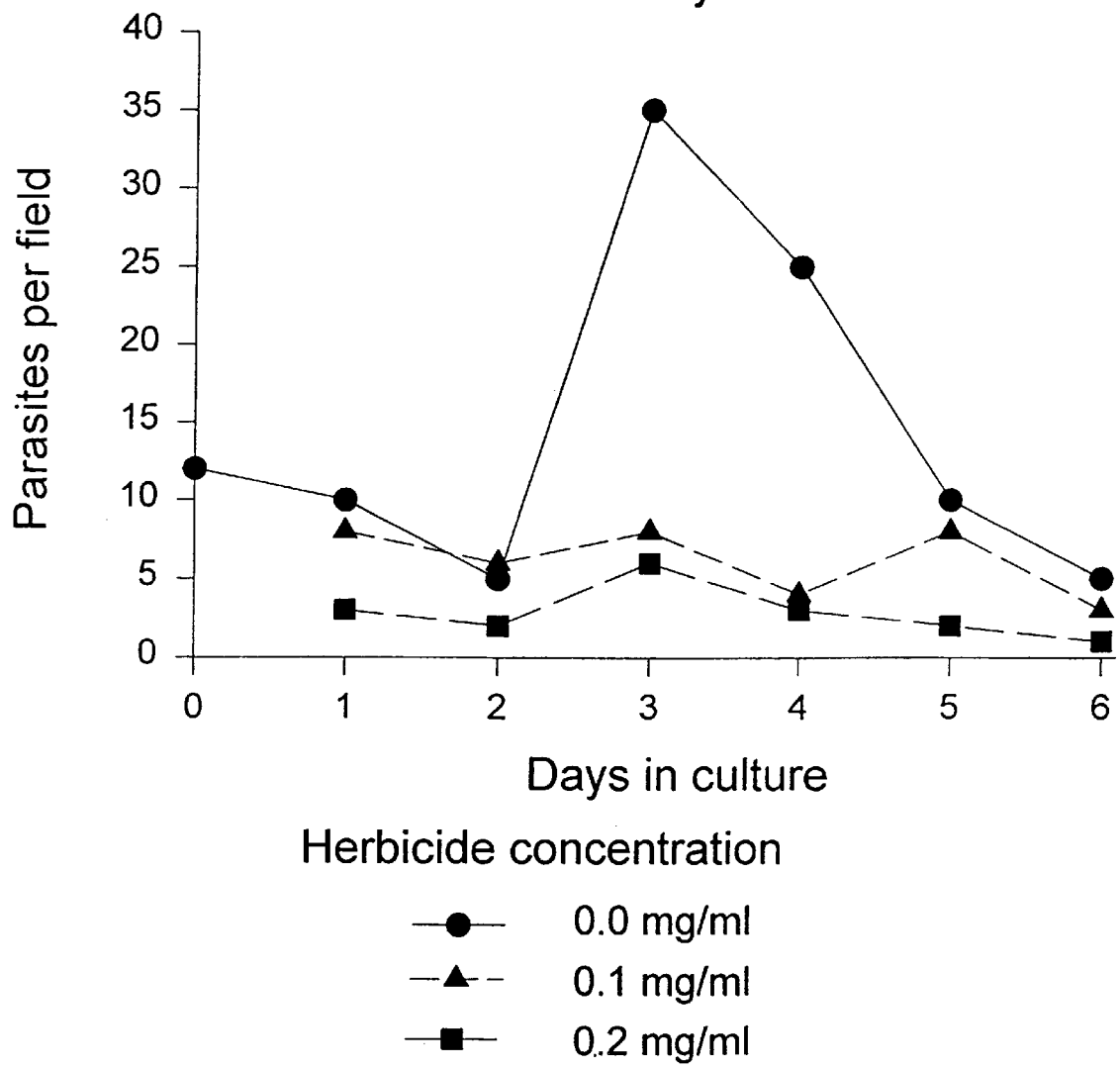

CAROTENOID SYNTHESIS INHIBITING HERBICIDES AND FATTY ACID SYNTHESIS INHIBITING OXIME HERBICIDES AS ANTI-APICOMPLEXA PROTOZOAN PARASITE AGENTS

This application is a division of application Ser. No. 08/847,932, filed Apr. 28, 1997.

BACKGROUND OF THE INVENTION

1. Field of the Invention

This invention relates to the use of chemical substances for the prevention and therapy of mammalian Apicomplexa protozoan parasitic infestations.

2. Description of Related Art

Protozoan parasites of the phylum Apicomplexa include the causative agents of the human disease malaria, as well as the agents of cattle diseases such as Texas cattle fever and East Coast fever. Furthermore, the causative agent of the human disease toxoplasmosis, *Toxoplasma gondii*, is also found in this phylum. Schmidt, G. D. and Roberts, L. S. *Foundations of Parasitology*. St. Louis, Times Mirror/Mosby, 1985. pp. 149, 173–178.

Malaria is one of the most important diseases of mankind. Two billion people are at risk of contracting malaria; over 200 million people are infected by the disease, and 3 million people die of malarial infection each year. The disease is caused by four species of plasmodia, *Plasmodium falciparum, Plasmodium vivax, Plasmodium ovale*, and *Plasmodium malariae*. Strains of the most common and most severe causative agent, *P. falciparum* have developed resistance to many of the current drugs used in treatment, and drug resistance has also been reported in *P. vivax*. Pudney, M. "Antimalarial: From Quinine to Atovaquone" in: Hunter, P. A., Darby, G. K. and Russell, N. J. *Fifty Years of Antimicrobial: Past Perspectives and Future Trends* (Cambridge, Society for General Microbiology, 53rd Symposium, 1995), pp. 229–247.

A 35-kb genome of plastid origin has been found in several of the Apicomplexa and it is through to be present in all protozoan species which are members of this phylum. Some Apicomplexa have been shown to be sensitive to members of certain triazine herbicides. This sensitivity is probably due to the interaction of the triazine herbicide with the D1 protein of the photosynthetic reaction center of these parasites organelles. Hackstein, J. H. P., Mackenstedt, U., Mehlhorn, H., Meijerink, J. P. P., Schubert, H., and Leunissen, J. A. M. Parasitic apicomplexans harbor a chlorophyll a-D1 complex, the potential target for therapeutic triazines. *Parasitology Research*, Vol. 81, (1995), pp. 207–216.

Further research has indicated the 35 kb extrachromosomal DNA of apicomplexan parasites is located in a novel organelle surrounded by four membranes. This suggests that the Apicomplexa parasites acquired this discrete organelle by secondary endosymboisis, probably of a green alga. Kohler, S., Delwiche, C. F., Denny, P. W., Tilney, L. G., Webster, P., Wilson, R. J. M., Palmer, J. D. and Roos, D. S. A Plastid of Probable Green Algal Origin in Apicomplexan Parasites. *Science*, Vol. 275, (Mar. 7, 1997), pp. 1485–1489.

Replication of the Apicomplexa protozoan parasite T. gondii has been found to be sensitive to inhibition by dinitroaniline herbicides at concentrations which do not inhibit host primary human fibroblasts. Such herbicides are known as specific and potent inhibitors of plant microtubules. Stokkermans, T. J. W., Schwartzman, J. D., Keenan, K., Morrissette, N. S., Tilney, L. G. and Roos, D. S. Inhibition of Toxoplasma gondii Replication by Dinitroaniline Herbicides. *Experimental Parasitology*, Vol. 84, (1996), pp. 355–370.

The prior art has disclosed the use of chemical agents belonging to the triazine class of herbicides as potential therapeutic agents. Such activity against some apicomplexan parasites is thought to result from interaction of the herbicide with the D1 protein of the photosynthetic reaction center of organelles of the parasites. In addition, dinitroaniline herbicides known to be inhibitors of plant microtubules also inhibit some apicomplexan parasites. The prior art, however, has not disclosed the use of herbicidal agents which inhibit carotenoid synthesis or certain herbicidal agents which inhibit fatty acid synthesis as inhibitors of apicomplexan parasites.

SUMMARY OF THE INVENTION

This invention is a process for treating a mammal infected with a protozoan parasite of the phylum Ampicomplexa with an herbicide of a type known to inhibit plant carotenoid biosynthesis. In particular, the carotenoid synthesis inhibiting herbicides fluridone and norflurazon, which are members of different chemical classes, have both been found effective against the multiplication of *Plasmodium falciparum* parasite in infected human red blood cells. Furthermore, this invention discloses the effectiveness against a protozoan parasite of the phylum Ampicomplexa of certain herbicides of the type known to inhibit plant fatty acid synthesis. In particular, the oxime cyclohexandione (CHO) herbicide sethoxydim has been found effective against the multiplication of *P. falciparum* parasite in infected human red blood cells. Other herbicides classed as aryloxyphenoxypropionic acids (APP) are known to also inhibit plant fatty acid synthesis. An APP herbicide, diclofop, however, has been found not to inhibit an Ampicomplexa parasite. The reason for this difference in behavior with respect to the parasites is not know, but it may depend on the effect of these two classes of fatty acid synthesis inhibiting herbicides on a second target site, as APP's have been proposed to also act on the plasma membrane of susceptible plants. Gronwald, J. W. Herbicides inhibiting acetyl-CoA carboxylase. *Biochemical Society Transactions*, vol. 22, (1994) pp. 618–620.

One objective of this invention is to provide anti-apicomplexa protozoan parasite agents of low toxicity to animals for use in treating parasitic infections.

Another objective is to provide anti-apicomplexa protozoan parasite agents which have a long shelf life, do not require cold storage, and are items of commerce.

A final objective is to provide new and additional therapeutic regimens useful against a scourge of mankind.

BRIEF DESCRIPTION OF THE DRAWINGS

FIG. 1 shows the effect of the 4-pyridone carotenoid synthesis inhibiting herbicide fluridone on the growth of *P. falciparum* in human red blood cells.

FIG. 2 shows the effect of the pyridazinone carotenoid synthesis inhibiting herbicide norflurazon on the growth of *P. falciparum* in human red blood cells.

FIG. 3 shows the effect of the APP, fatty acid synthesis inhibiting, herbicide diclofop on the growth of *P. falciparum* in human red blood cells.

FIG. 4 shows the effect of the oxime CHO, fatty acid synthesis inhibiting, herbicide sethoxydim on the growth of *P. falciparum* in human red blood cells.

DESCRIPTION OF THE PREFERRED EMBODIMENTS

The herbicides fluridone and norflurazon are known to be representatives of several classes of chemicals which act as carotenoid synthesis inhibiting herbicides. Worthing, C. R. The Pesticide Manual. Farnham, Surrey, British Crop Protection Council, 1991, pp. 418, 624. These herbicides were tested for effect on the growth of the Ampicomplexa protozoan parasite *Plasmodium falciparum* in human red blood cells as in Examples 1 and 2 and FIGS. 1 and 2. Each carotenoid synthesis inhibiting herbicide herbicide, fluridone and norflurazon, were shown to be effective inhibitors of the Ampicomplexa parasite.

The APP herbicides diclofop, haloxyfop, quozalofop, etc. and the CHO or oxime herbicides sethoxydim, alloxydim, cycloxydim, clethodim, tralkoxydim etc. appear to act primarily through inhibition of fatty acid synthesis through inhibition of acetyl-CoA carboxylase. Worthing, C. R. The Pesticide Manual. Farnham, Surrey, British Crop Protection Council, 1991, pp 21, 175, 197, 262, 761, 828. Gronwald, J. W. Herbicides inhibiting acetyl-CoA carboxylase. *Biochemical Society Transactions*, vol. 22, (1994) pp. 618–620. The APP herbicide diclofop was found not to inhibit the growth of the Ampicomplexa parasite *P. falciparum* in human red blood cells, as shown in Example 3 and FIG. 3. The oxime CHO herbicide sethoxydim was found to inhibit the growth of the Ampicomplexa parasite *P. falciparum* in human red blood cells, as shown in Example 4 and FIG. 4.

Without wishing to be held to this explanation, it is proposed that the difference in behavior between the two classes of fatty acid inhibitory herbicides, the CHO's and the APP's, reported in the above paragraph may be due to a secondary target site for the APP diclofop herbicide. It has been proposed that diclofop, in addition to its effect on acetyl-CoA carboxylase, may interact with a plasma membrane protein that regulates transmembrane proton movement. Gronwald, J. W. Herbicides inhibiting acetyl-CoA carboxylase. *Biochemical Society Transactions*, vol. 22, (1994) pp. 618–620.

Any method of administration used to treat mammalian species including humans with therapeutic drugs may be used to administer the therapeutic herbicides of this invention to humans and other mammalian species infected with Ampicomplexa protozoan parasites. The herbicides may be formulated with pharmacologically suitable additives such as excipients, flavorings, colorings, and preservatives. The herbicides may be administered per os in the form of liquids, capsules, or pills. The herbicides may be administered by intramuscular, intraperitoneal, or intravenous injection. The herbicides may be administered topically as salves. A suitable dose for an infected mammal is in the range of 0.001 to 1.0 gram/kg body weight per day.

Example 1

Effect of Fluridone on Growth of *P. falciparum* in Human Red Blood Cells

A complete medium for growing *P. falciparum* was prepared as follows: RPMI 1640 liquid medium containing hepes buffer, sodium bicarbonate, and L-glutamine, GIBCO catalog number 22400-010, was obtained from GIBCO, Grand Island, N.Y. The medium was supplemented with hypoxanthine at a concentration of 0.0033 gm hypoxanthine per 500 ml RPMI 1640 and human type O serum at 50 ml serum per 500 ml RPMI 1640 medium. The serum had been screened for hepatitis B, hepatitis C, HIV and syphilis and was obtained from Interstate Blood Bank, Memphis, Tenn. Human male type O positive red blood cells (RBC) were washed three times in RPMI 1640 medium and were added at a concentration of 50% of the RBC content of whole blood. *P. falciparum* parasites were added at a volume of 5 ml of parasitized RBC cultures where the absolute number of parasites added per culture is variable between experiments. There is, however, no variability in number of parasites added per culture within an experiment. The hematocrit of the added parasite containing RBC cultures was 5%. Prior to the addition of the 5 ml parasite containing RBC culture, it was transferred to a 15 ml clinical centrifuge tube and centrifuged at 1600 rpm in a clinical centrifuge. The resulting supernatant fluid was drawn off and the packed parasitized RBC were added to the culture system.

The cultures were placed in tubes in duplicate and herbicide was dissolved in ethanol, diluted, and added at indicated final concentrations. In this Example 1, the herbicide fluridone was obtained as catalogue PS 1070 from Chem Service, Inc. 660 Tower Lane, West Chester, Pa. and was used. The cultures were incubated at 37° C. The cultures were sampled at the indicated days after inoculating with parasites for up to 20 days in a bell jar where the oxygen concentration was less than 5%. For sampling, each culture was put on a slide as a blood film and allowed to dry. The slides were stained with Giemsa stain and observed microscopically using an oil immersion objective lens at approximately 1000 times magnification. Approximately 25 fields were examined for each sample. The number of red blood cells infected with *P. falciparum* was determined and expressed as an average number of parasite infected RBCs per field.

FIG. 1 shows the effect of fluridone at concentrations of 0.2, 0.1 and 0 mg/mi on *P. falciparum*. Fluridone at 0.2 mg/ml inhibited the growth of the parasite. No effects of fluridone on the human RBCs were observed at any concentration. However, a striking decrease in the number of parasite infected RBCs was observed when the concentration of this herbicide was 0.2 mg/ml or higher. Specifically, the increase in the number of parasitized RBC which is typically noted during the initial 3–6 days in this assay system was inhibited. Increasing parasite infected RBC numbers apparent in the control (0 mg/ml) and lower herbicide concentration samples (0.1 mg/ml) over the initial 3–6 days of culture were absent at fluridone concentrations of 0.2 mg/ml and above. Fresh RPMI 1640 media was not added to the cultures so that additional rounds of infection were not observed quantitatively.

Example 2

Effect of Norflurazon on Growth of *P. falciparum* in Human Red Blood Cells.

FIG. 2 shows the effect of norflurazon at concentrations of 0.5, 0.1 and 0 mg/ml on *P. falciparum* determined under the conditions of Example 1. Norflurazon was obtained as catalogue No. PS 1044 from Chem Service, Inc. 660 Tower Lane, West Chester, Pa. and was used in this Example. Norflurazon at 0.5 and 0.1 mg/ml inhibited the growth of the parasite with a pattern similar to that observed in Example 1.

Example 3

Effect of Diclofop on Growth of *P. falciparum* in Human Red Blood Cells.

FIG. 3 shows the effect of diclofop at concentrations of 0.4, 0.2 and 0 mg/mi on *P. falciparum* determined under the conditions of Example 1. Diclofopmethyl was obtained as catalogue No. PS 1036 from Chem Service, Inc. 660 Tower Lane, West Chester, Pa. and was used in this Example. Diclofop did not inhibit the growth of the parasite at any of the concentrations tested. The increase in parasitized RBC at 3–6 days observed in the control samples was also observed in all of the experimental samples.

Example 4

Effect of Sethoxydim on Growth of *P. falciparum* in Human Red Blood Cells.

FIG. 4 shows the effect of sethoxydim at concentrations of 0.2, 0.1, and 0 mg/ml on *P. falciparum* determined under the conditions of Example 1. Sethoxydim was obtained as catalogue No. PS 2013 from Chem Service, Inc. 660 Tower Lane, West Chester, Pa. and was used in this Example. Sethoxydim at 0.2 and 0.1 mg/mi inhibited the growth of the parasite with a pattern similar to that observed in Example 1.

It will be apparent to those skilled in the art that the examples and embodiments described herein are by way of illustration and not of limitation, and that other examples may be used without departing from the spirit and scope of the present invention, as set forth in the appended claims.

We claim:

1. The process of treating a mammalian species infected with a parasite of the genus Plasmodium comprising the step:

administering to said mammalian species an effective amount of cyclohexandione oxime herbicidal agent.

2. The process of claim 1 wherein the herbicide is selected from the group of cyclohexandione oxime herbicides consisting of sethoxydim, tralkoxydim, alloxydim, clethodim and cycloxydim.

3. The process of claim 1 wherein the herbicide is sethoxydim.

4. The process of claim 1 wherein said mammalian species is a human.

5. The process of claim 1 wherein said parasite is one or more of the group of parasites consisting of *Plasmodium falciparum, Plasmodium vivax, Plasmodium ovale*, and *Plasmodium malariae*.

6. The process of claim 1 wherein said parasite is *Plasmodium falciparum*.

* * * * *